United States Patent [19]

Jones et al.

[11] 4,358,457
[45] Nov. 9, 1982

[54] TETRAHYDRO-7a-(OPTIONALLY SUBSTITUTED PHENYL)-1H-PYRROLO[1,2-b][1,2,4]-TRIAZOLE-2(3H)-THIONES

[75] Inventors: Winton D. Jones; John M. Kane, both of Cincinnati; Francis P. Miller, Loveland, all of Ohio

[73] Assignee: Merrell Dow Pharmaceuticals Inc., Cincinnati, Ohio

[21] Appl. No.: 286,950

[22] Filed: Jul. 27, 1981

[51] Int. Cl.³ .................... A61K 31/41; C07D 487/04
[52] U.S. Cl. .................................... 424/269; 424/232; 548/263; 564/18; 568/335
[58] Field of Search ......................... 548/263; 424/269

[56] References Cited
FOREIGN PATENT DOCUMENTS 5335M 8/1967 France ................................. 548/263
811765 4/1959 United Kingdom ................ 548/263
649719 5/1979 U.S.S.R. .............................. 548/263

Primary Examiner—Alton D. Rollins
Attorney, Agent, or Firm—John J. Kolano; Gary D. Street; Raymond A. McDonald

[57] ABSTRACT

Compounds of the formula

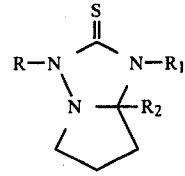

wherein R is H or $C_{1-5}$ straight or branched chain alkyl; $R_1$ is H, $C_{1-10}$ straight or branched chain alkyl, allyl or phenyl; and $R_2$ is phenyl or phenyl substituted with F, Cl, $C_{1-5}$ straight or branched chain alkyl, di-F, di-Cl or di-Br; and the pharmaceutically acceptable acid addition salts thereof; are useful as muscle relaxants, anticonvulsants and analgesics.

5 Claims, No Drawings

TETRAHYDRO-7a-(OPTIONALLY SUBSTITUTED PHENYL)-1H-PYRROLO[1,2-b][1,2,4]-TRIAZOLE-2(3H)-THIONES

The present invention relates to tetrahydro-7a-(optionally substituted phenyl)-1$\underline{H}$-pyrrolo[1,2-b][1,2,4]-triazole-2(3$\underline{H}$)-thiones having the following formula:

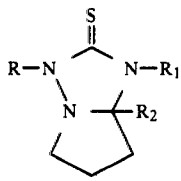

wherein R is H or $C_{1-5}$ straight or branched chain alkyl; $R_1$ is H, $C_{1-10}$ straight or branched chain alkyl, allyl or phenyl; and $R_2$ is phenyl or phenyl substituted with F, Cl, $C_{1-5}$ straight or branched chain alkyl, di-F, di-Cl or di-Br; and the pharmaceutically acceptable acid addition salts thereof. The compounds are useful as muscle relaxants, anticonvulsants and analgesics.

DETAILED DESCRIPTION OF THE INVENTION

Illustrative examples of straight or branched chain $C_{1-10}$ alkyl groups which $R_1$ may represent as used herein include, for example, methyl, ethyl, n-propyl, isopropyl, n-butyl, sec-butyl, isobutyl, tert-butyl, n-pentyl, isopentyl, neopentyl, n-hexyl, isohexyl, n-heptyl, isoheptyl, n-octyl, isooctyl, n-nonyl, isononyl, n-decyl, isodecyl, etc. Illustrative examples of straight or branched chain $C_{1-5}$ alkyl groups mentioned in describing the groups R and $R_2$ include, for example, the corresponding examples mentioned above.

Pharmaceutically acceptable acid addition salts of the compounds of the present invention include those of any suitable inorganic or organic acid. Suitable inorganic acids are, for example, hydrochloric, hydrobromic, sulfuric or phosphoric acid. Suitable organic acids are, for example, carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic and 2-phenoxybenzoic, or sulfonic acids such as, for example, methanesulfonic and 2-hydroxyethane-sulfonic acid.

Of the compounds of the present invention, the preferred compounds include 5,6,7,7a-tetrahydro-1-methyl-7a-phenyl-1$\underline{H}$-pyrrolo[1,2-b][1,2,4]triazole-2(3$\underline{H}$)-thione and its acid addition salts.

Illustrative examples of compounds of this invention include those wherein each of R and $R_1$ is H or $C_{1-5}$ alkyl, e.g., $CH_3$. These include, for example, 7a-(4-chlorophenyl)-5,6,7,7a-tetrahydro-1-methyl-1$\underline{H}$-pyrrolo[1,2-b]-[1,2,4]triazole-2(3$\underline{H}$)-thione, 5,6,7,7a-tetrahydro-1-methyl-7a-phenyl-1$\underline{H}$-pyrrolo[1,2-b][1,2,4]triazole-2(3$\underline{H}$)-thione, 5,6,7,7a-tetrahydro-1-(2-propenyl)-7a-phenyl-1$\underline{H}$-pyrrolo[1,2-b][1,2,4]-triazole-2(3$\underline{H}$)-thione, 5,6,7,7a-tetrahydro-1,7a-diphenyl-1$\underline{H}$-pyrrolo[1,2-b][1,2,4]triazole-2(3$\underline{H}$)-thione, and 7a-(4-methylphenyl)-5,6,7,7a-tetrahydro-1-methyl-1$\underline{H}$-pyrrolo[1,2-b][1,2,4]triazole-2(3$\underline{H}$)-thione.

The compounds of this invention are useful as muscle relaxants, anticonvulsants and analgesics. For analgesic activity, those compounds wherein $R_2$ is phenyl are preferred. These compounds can be administered to warm-blooded animals, mammals, rats, mice, dogs, cats, horses, pigs, cows, sheep and humans. As used herein, the term "patient" is intended to mean the animal or mammal being treated.

The muscle-relaxant, anticonvulsant and analgesic activity of the compounds of this invention may be illustrated by their effectiveness in standard pharmacological screening tests. For example, anticonvulsant efficacy may be demonstrated by inhibition of clonic seizures induced by injection of metrazole in mice (metrazole antagonism test); analgesic efficacy may be demonstrated by inhibition of writhing or squirming upon administration of acetic acid in mice (antagonism of acetic acid writhing test) or by an increase in the reaction time for tail withdrawal after application of radiant heat in rats (rat tail flick test); and muscle-relaxing efficacy may be demonstrated by antagonism of decerebrate rigidity in rats.

The compounds of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules and pills, or liquid solutions, suspensions or emulsions for oral and parenteral administration. The dosage unit administered can be any muscle-relaxing, anticonvulsant or analgesic effective amount. The quantity of compounds administered can vary over a wide range to provide from about 12 to about 100 mg/kg of body weight of the patient per day, to achieve the desired effect for all uses. Unit doses can contain about 5–500 mg of a compound of the present invention and may be administered, for example, from 1 to 4 times daily.

The compounds of the present invention are prepared by reacting a 1-$R_2$-4-halo-butan-1-one of the formula

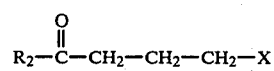

wherein X is Cl or Br, with a substituted thiosemicarbazide of the formula

wherein R, $R_1$ and $R_2$ are as hereinbefore defined. The reaction is generally conducted in the presence of a solvent, e.g., a lower alkanol, such as, methanol, ethanol, isopropanol, n-propanol, n-butanol and the like, preferably isopropanol. The reaction time may vary from about 4 hours to about 48 hours, depending upon the reactants, the solvent and the reaction temperature which may vary from about 60° C. to about 80° C., preferably around 78° C. The product is generally worked-up by permitting the reaction mixture to cool and then concentrating it in vacuo. The residue, usually an oil, is dissolved in a solvent such as $CH_2Cl_2$, washed with, e.g., $H_2O$ and 10% NaOH, dried, (e.g, with $MgSO_4$), filtered and concentrated in vacuo. Trituration, e.g, with diethyl ether, yields the solid pyrrolotriazole of the present invention. The solid is recrystallized from an appropriate solvent, e.g., a mixture of a lower alkanol with, e.g, acetone, butanone or ethylacetate, e.g., methanol/acetone or methanol/ethylacetate, producing the compound of the present invention. The acid addition salt, e.g., hydrochloride, can be formed by the addition of a stoichiometric or slight excess of the selected acid in anhydrous form to a solution of the free base in e.g., an anhydrous lower alkanol.

Both the 1-$R_2$-4-halo-butan-1-one and the substituted thiosemicarbazide which are employed as starting materials in the preparation of the compounds of the present invention are either commercially available or, when unavailable, are very readily preparable by standard chemical reactions which are well-known to those of ordinary skill in the art. For example, the butanones may be prepared by reacting the corresponding optionally substituted benzene with a halobutanoyl halide, e.g., chlorobutanoyl chloride, via a Friedel-Crafts reaction using an aluminum trichloride catalyst, e.g., to prepare the corresponding 1-$R_2$-4-halo-butan-1-one. The substituted thiosemicarbazides may be prepared by conventionally reacting the appropriate substituted isothiocyanate with a hydrazine derivative in a solvent, e.g., ethanol.

EXAMPLES

The following examples are illustrative of the invention.

EXAMPLE 1

7a-(4-Chlorophenyl)-5,6,7,7a-tetrahydro-1-methyl-1H-pyrrolo[1,2-b][1,2,4]triazole-2(3H)-thione 21.7 g (0.1 mole) of 1-(4-chlorophenyl)-4-chlorobutan-1-one and 10.51 g of (0.1 mole) of 4-methyl-thiosemicabazide are heated and stirred at reflux in 200 ml of ethanol overnight. The yellow ethanolic solution is concentrated in vacuo to an oil. The oil is dissolved in methylene chloride and extracted with 8% KOH. It is then separated and dried (MgSO$_4$). After filtration and concentration, a first oil is produced. The solution is further concentrated to yield a second brown oil. The latter oil is triturated with 200 ml of diethyl ether and the yellow diethyl ether layer is decanted. After standing overnight, tan colored cubes are deposited from the diethyl ether layer. The cubes are collected on a filter. A white powder is then deposited from the filtrate. Analysis shows that the two products are the same. Recrystallization of the combined products from methylene chloride/hexane and subsequent drying under high vacuum yield 7a-(4-chlorophenyl)-5,6,7,7a-tetrahydro-1-methyl-1H-pyrrolo[1,2-b][1,2,4]triazole-2(3H)-thione. M.p. 159°–161° C.

EXAMPLE 2

5,6,7,7a-Tetrahydro-1-methyl-7a-phenyl-1H-pyrrolo[1,2-b][1,2,4]triazole-2(3H)-thione 4.2 g of 4-methyl-thiosemicarbazide and 8.0 g of 1-phenyl-4-chlorobutan-1-one in 200 ml of isopropanol is refluxed for 48 hours. The solvent is then evaporated and the residue is dissolved in methylene chloride. The resulting solution is washed with saturated aqueous sodium bicarbonate and with saturated aqueous sodium chloride and then dried over sodium sulfate. Evaporation of the solvent leaves a brownish oil which crystallizes partially. This is treated with ether to give a light yellow powder which is purified by flash chromatography, using 10% ethyl acetate/methylene chloride as the eluent to give 5,6,7,7a-tetrahydro-1-methyl-7a-phenyl-1H-pyrrolo[1,2-b][1,2,4]triazole-2(3H)-thione as colorless crystals melting at about 148°–151° C.

EXAMPLE 3

5,6,7,7a-Tetrahydro-1,3-dimethyl-7a-phenyl-1H-pyrrolo[1,2-b][1,2,4]triazole-2(3H)-thione A solution of 4.0 g of 2,4-dimethyl-thiosemicarbazide and 6.7 g of 1-phenyl-4-chlorobutan-1-one in 165 ml of isopropanol is refluxed for 48 hours. The mixture is then allowed to cool to room temperature and stirred for an additional 48 hours. The solvent is evaporated, the residue is dissolved in methylene chloride, and the methylene chloride solution is washed with saturated aqueous sodium bicarbonate and with saturated aqueous sodium chloride and dried over sodium sulfate. Evaporation of the solvent leaves a brownish oil which crystallizes and is treated with hexane. The resulting greyish powder is purified by flash chromatography using 4% ethyl acetate/methylene chloride as eluent, followed by crystallization from hexane to give 5,6,7,7a-tetrahydro-1,3-dimethyl-7a-phenyl-1H-pyrrolo[1,2-b][1,2,4]triazole-2(3H)-thione as tiny colorless needles melting at about 83°–85° C.

EXAMPLES 4–6

Analogously to the procedure of Example 1, 5,6,7,7a-tetrahydro-1-(2-propenyl-1H-pyrrolo[1,2-b][1,2,4]triazole-2(3H)-thione, 5,6,7,7a-tetrahydro-1,7a-diphenyl-1H-pyrrolo[1,2-b][1,2,4]triazole-2(3H)-thione, 7a-(4-methylphenyl)-tetrahydro-1-methyl-1H-pyrrolo[1,2-b][1,2,4]triazole-2(3H)-thione are prepared by reacting, respectively, 4-allyl-thiosemicarbazide with 1-phenyl-4-chloro-butan-1-one, 4-phenyl-thiosemicarbazide with 1-phenyl-4-chlorobutan-1-one and 4-methyl-thiosemicarbazide with 1-(4-methylphenyl)-4-chlorobutan-1-one.

EXAMPLE 7

An illustrative composition for tablets is as follows:

|     |                                                                                            | Per Tablet |
| --- | ------------------------------------------------------------------------------------------ | ---------- |
| (a) | 5,6,7,7a-Tetrahydro-1-methyl-7a-phenyl-1H-pyrrolo[1,2-b][1,2,4]-triazole-2(3H)-thione      | 100.0 ml   |
| (b) | Wheat starch                                                                               | 15.0 mg    |
| (c) | Lactose                                                                                    | 33.5 m     |
| (d) | Magnesium stearate                                                                         | 1.5 mg     |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

EXAMPLE 8

An illustrative composition for a parenteral injection is the following wherein the quantities are on a weight to volume basis.

|     |                                                                                            | Amount   |
| --- | ------------------------------------------------------------------------------------------ | -------- |
| (a) | 5,6,7,7a-Tetrahydro-1-methyl-7a-phenyl-1H-pyrrolo[1,2-b][1,2,4]-triazole-2(3H)-thione      | 100.0 mg |
| (b) | Sodium chloride                                                                            | q.s.     |
| (c) | Water for injection to make                                                                | 20 ml    |

The composition is prepared by dissolving the active ingredient (a) and sufficient sodium chloride in water for injection to render the solution isotonic. The composition may be dispensed in a single ampoule containing 100 mg of the active ingredient for multiple dosage or in 20 ampoules for single dosage.

EXAMPLE 9

An illustrative composition for hard gelatin capsules is as follows:

|     |                                                                                   | Amount   |
| --- | --------------------------------------------------------------------------------- | -------- |
| (a) | 5,6,7,7a-Tetrahydro-1-methyl-7a-phenyl-1H-pyrrolo[1,2-b][1,2,4]-triazole-2(3H)-thione | 200.0 mg |
| (b) | Talc                                                                              | 35.0 mg  |

The composition is prepared by passing the dry powders of (a) and (b) through a fine mesh screen and mixing them well. The powder is then filled into No. 0 hard gelatin capsules at a net fill of 235 mg per capsule.

EXAMPLE 10

An illustrative composition for pills is the following:

|     |                                                                                   | Per Pill |
| --- | --------------------------------------------------------------------------------- | -------- |
| (a) | 5,6,7,7a-Tetrahydro-1-methyl-7a-phenyl-1H-pyrrolo[1,2-b][1,2,4]-triazole-2(3H)-thione | 200 mg   |
| (b) | Corn starch                                                                       | 130 mg   |
| (c) | Liquid glucose                                                                    | 20 ml    |

The pills are prepared by blending the active ingredient (a) and the corn starch; then adding the liquid glucose with thorough kneading to form a plastic mass from which the pills are cut and formed.

EXAMPLE 11

The compounds of the preceding examples each can be administered to achieve one or more of skeletal muscle relaxation, an anticonvulsion effect and analgesia in a patient in which a muscle relaxing effect, protection against seizures or an analgesic effect is desired, e.g., a patient suffering from a muscle spasm, clinical spasticity from upper motor nervous disorders, e.g., spinal cord injury, stroke, cerebral palsy, multiple sclerosis, paraplegia, stiff-man syndrome and tetanus; a patient being treated for status epilepticus, or severe recurrent convulsive, petit or grand mal or psychomotor seizures; or a patient suffering from pain. Muscle relaxation is inducible in rats by administration parenterally (i.v.) similarly to chlordiazepoxide (Librium).

We claim:

1. A compound of the formula

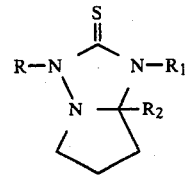

wherein R is H or $C_{1-5}$ straight or branched chain alkyl; $R_1$ is H, $C_{1-10}$ straight or branched chain alkyl, allyl or phenyl; and $R_2$ is phenyl or phenyl substituted with F, Cl, $C_{1-5}$ straight or branched chain alkyl, di-F, di-Cl or di-Br; and the pharmaceutically acceptable acid addition salts thereof.

2. 5,6,7,7a-Tetrahydro-1-methyl-7a-phenyl-1H-pyrrolo[1,2-b][1,2,4]triazole-2(3H)-thione, a compound of claim 1.

3. 7a-(4-Chlorophenyl)-5,6,7,7a-tetrahydro-1-methyl-1H-pyrrolo[1,2-b][1,2,4]triazole-2(3H)-thione, a compound of claim 1.

4. A pharmaceutical composition comprising in unit dosage form about 5–500 mg of a compound of claim 1 and a significant amount of a pharmaceutically acceptable carrier.

5. A process for preparing a compound of the formula

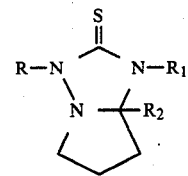

wherein R is H or $C_{1-5}$ straight or branched chain alkyl; $R_1$ is H, $C_{1-10}$ straight or branched chain alkyl, allyl or phenyl; and $R_2$ is phenyl or phenyl substituted with F, Cl, $C_{1-5}$ straight or branched chain alkyl, di-F, di-Cl or di-Br; and the pharmaceutically acceptable acid addition salts thereof, which comprises (a) reacting a 1-$R_2$-4-halo-butan-1-one of the formula

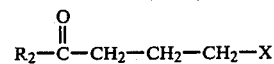

with a substituted thiosemicarbazide of the formula

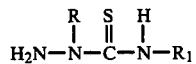

wherein X is Cl or Br and R, $R_1$ and $R_2$ are as defined above; or (b) reacting a free amine produced by (a) with a pharmaceutically acceptable acid to produce the corresponding acid addition salt.

* * * * *